US012778132B2

(12) United States Patent
Beifort

(10) Patent No.: US 12,778,132 B2
(45) Date of Patent: Nov. 3, 2026

(54) BIOLOGICAL AGENT FOR THE PREVENTION AND TREATMENT OF LEAF DISEASES IN PLANTS, WHICH ARE CAUSED BY BIOTROPHIC OR HEMIBIOTROPHIC FUNGI

(71) Applicant: ABITEP GmbH, Berlin (DE)

(72) Inventor: Paul Beifort, Berlin (DE)

(73) Assignee: ABITEP GMBH, Berlin (DE)

( * ) Notice: Subject to any disclaimer, the term of this patent is extended or adjusted under 35 U.S.C. 154(b) by 512 days.

(21) Appl. No.: 18/121,356

(22) Filed: Mar. 14, 2023

(65) Prior Publication Data

US 2023/0284630 A1 Sep. 14, 2023

(30) Foreign Application Priority Data

Mar. 14, 2022 (DE) ........................ 102022105868.9

(51) Int. Cl.
*A01N 63/20* (2020.01)
*A01P 3/00* (2006.01)
*C12N 1/205* (2026.01)

(52) U.S. Cl.
CPC ................ *A01N 63/20* (2020.01); *A01P 3/00* (2021.08); *C12N 1/205* (2021.05)

(58) Field of Classification Search
CPC ............ A01N 63/20; A01P 3/00; C12N 1/205
See application file for complete search history.

(56) References Cited

U.S. PATENT DOCUMENTS

2010/0267790 A1* 10/2010 Voeste ............... A01N 2300/00 514/384
2021/0123043 A1* 4/2021 Wigley .................. A01N 63/27

FOREIGN PATENT DOCUMENTS

WO WO-2021257718 A2 * 12/2021 ............ A01N 63/25

OTHER PUBLICATIONS

Chen et al. Complete Genome Sequence of Kosakonia radicincitans GXGL-4A, a Nitrogen-Fixing Bacterium with Capability to Degrade TEX. Curr Microbiol. Aug. 2020;77(8):1848-1857. doi: 10.1007/s00284-020-01942-3 (Year: 2020).*

Agarwal et al. ("Differential antagonistic responses of Bacillus pumilus MSUA3 against Rhizoctonia solani and Fusarium oxysporum causing fungal diseases in Fagopyrum esculentum Moench." Microbiological research 205 (2017): 40-47) (Year: 2017).*

Berger et al. "Successful formulation and application of plant growth-promoting Kosakonia radicincitans in maize cultivation." BioMed research international 2018.1 (2018): 6439481 (on IDS filed Aug. 1, 2023) (Year: 2018).*

Robles-Yerena, Leticia, et al. "First report of Cladosporium cladosporioides causing leaf spot on tomato in Mexico." Journal of Plant Pathology 101.3 (2019): 759-759. (Year: 2019).*

Brock et al. "Impact of the PGPB Enterobacter radicincitans DSM 16656 on growth, glucosinolate profile, and immune responses of *Arabidopsis thaliana*." Microbial Ecology 65.3 (2013): 661-670 (on IDS filed Aug. 1, 2023) (Year: 2013).*

Berger et al. "Successful formulation and application of plant growth-promoting Kosakonia radicincitans in maize cultivation." BioMed research international Jan. 2018 (2018): 6439481 (on IDS filed Aug. 1, 2023) (Year: 2018).*

Lambrese et al. "Production of siderophores by the bacterium Kosakonia radicincitans and its application to control of phytopathogenic fungi." Bioresource Technology Reports 3 (2018): 82-87, (on IDS filed Feb. 6, 2025). (Year: 2018).*

Extended European Search Report from EP Serial No. 23152855.5, mailed Jun. 26, 2023, 14 pages.

Cruz Barrera Mauricio et al; "Salt stress and hydroxyectoine enhance phosphate solubilization and plant colonization capacity of Kosakonia radicincitans", Journal of Advance Research, Elsevier, Amsterdam, NL, Bd. 19,1; Sep. 2019, pp. 91-97.

Brock, Anita K et al.; "Plant growth-promoting bacteria *Kosakonia radicincitans* mediate anti-herbivore defense in *Arabidopsis thaliana*", Planta, Springer Berlin Heidelberg, Bd. 248, Nr. 6; Aug. 17, 2018, pp. 1383-1392.

Berger Beatrice et al.; "Successful Formulation and Application of Plant Growth-Promoting Kosakonia radicincitans in Maize Cultivation", Biomed Research International, Bd. 2018, 28, Mar. 28, 2018, pp. 1-8.

Berger Beatrice et al; "The plant growth-promoting bacterium *Kosakonia radicincitans* improves fruit yield and quality of Solanum lycopersicum", Journal of the Science of Food and Agriculture, Bd. 97, Nr. 14, Oct. 17, 2017, pp. 4865-4871.

Brock Anita K. et al.; "Impact of PGPB Enterobacter radicincitans DSM 16656 on Growth, Glucosinolate Profile, and Immune Responses of *Arabidopsis thaliana*", Microbial Ecology, Bd. 65, Nr. 3, Apr. 1, 2013, pp. 661-670.

Navarta Leonard G. et al.; "Freeze-drying of a mixture of bacterium and yeast for application in postharvest control of pathogenic fungi", SN Applied Sciences, Bd. 2, Nr. 7, Jul. 1, 2020, p. 1223.

Koch Eckhard et al; "Neue Behandlungsverfahren für Maissaatgut", MAIS, Feb. 1, 2018, pp. 60-63.

EP Communication under Article 94(3) EPC, in European Application No. 23152855.5, maild Nov. 13, 2024, 21 pages with English translation.

(Continued)

*Primary Examiner* — Anand U Desai
*Assistant Examiner* — Andrew T Moehlman
(74) *Attorney, Agent, or Firm* — Ray Quinney & Nebeker P.C.; Paul N. Taylor

(57) ABSTRACT

The present invention concerns the preparation and use of an agent for the prevention and treatment of leaf diseases in plants caused by living biotrophic and hemibiotrophic fungal pathogens, wherein the agent contains the bacterium *Kosakonia radicincitans*.

6 Claims, 2 Drawing Sheets

(56) References Cited

OTHER PUBLICATIONS

Figure 1:
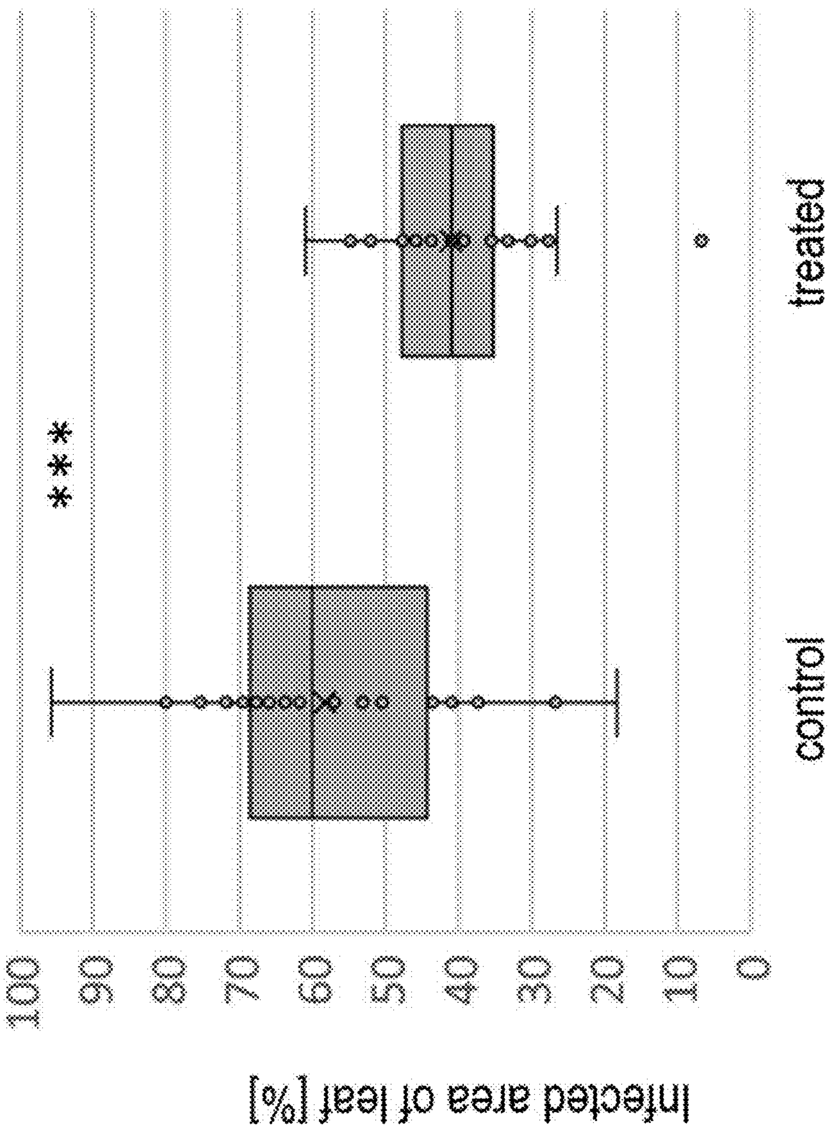

Lambrese Y. et al., "Production of siderophores by the bacterium *Kosakonia radicincitans* and its application to control of phytopathogenic fungi", Bioresource Technology Reports (3), Published Jul. 3, 2018, pp. 82-87.

Berger, B. [u.a.]: Successful Formulation and Application of Plant Growth-Promoting Kosakonia radicincitans in Maize Cultivation. In: BioMed Res. Int., 2018, Artikel-Id. 643948.—ISSN 2314-6141.

Berger, B. [u.a.]: The plant growth-promoting bacterium *Kosakonia radicincitans* improves fruit yield and quality of Solanum lycopersicum. In: J. Sci. Food Agric., Bd. 97, 2017, Nr. 14, S. 4865-4871.—ISSN 0022-5142.

FiBL (Hrsg.): Betriebsmittelliste 2018 für den ökologischen Landbau in Deutschland. Frankfurt: Lokay. ISBN 978-3-03736-056-9. genannt.

10 2022 105 868.9, Oct. 13, 2022, German Office Action.

* cited by examiner

BIOLOGICAL AGENT FOR THE PREVENTION AND TREATMENT OF LEAF DISEASES IN PLANTS, WHICH ARE CAUSED BY BIOTROPHIC OR HEMIBIOTROPHIC FUNGI

SUBJECT MATTER OF THE INVENTION

The invention relates to an environmentally friendly, effective biological agent based on beneficial endophytic bacteria of the species *Kosakonia radicincitans* in order to protect cultivated plants against fungal leaf diseases which are caused by biotrophic or hemibiotrophic fungi. These include the pathogens of rust diseases, for example soybean rust (*Phakopsora pachyrhizi*), grain rust (*Puccinia* sp.), vegetable rust (*Puccinia* sp.), leaf spot diseases, for example *Septoria* sp., and true and false powdery mildews, for example *Peronospora* sp. or *Plasmopara* sp.

Members of the species *Kosakonia radicincitans* have the ability to carry out root and endophytic colonization of cultivated plants. The subject matter of the invention is a biological agent which is used as a seed stock treatment and/or leaf treatment for protection against leaf diseases.

The fields of application of the invention are plant protection, agriculture and horticulture.

Introduction

The biological control of leaf diseases caused by phytopathogenic fungi is urgently needed in order to meet the increasing need for ecologically harmlessly-produced agricultural products. Despite the social change in recent years regarding the legal requirements for licensing plant protection agents, to a large extent, current practices in agriculture are still based on the use of synthetic pesticides, the genetic resistance of host plants and an appropriate management of plants and the environment. It is precisely the ongoing use of synthetic agents with a simple mechanism of action which means that over time, they lose their efficacy, generate resistances to the pathogens and often have an adverse effect on the environment. Biotrophic and hemibiotrophic fungi have proved to be particularly imperishable, and controlling them has turned out to be difficult because they propagate to a certain extent in the interior of the leaf and often cannot be reached by plant protection agents which are applied externally.

The fungal pathogens of leaf diseases are members of a very wide variety of genuses of fungi. A common factor with them is that they are capable of colonizing the leaf surface or the interior of the leaf and can therefore penetrate into the leaf. A further common factor is that the infection with the fungal pathogen is associated with an optical change in the leaf as the plant grows.

In general, fungal diseases of the leaf can be distinguished on the basis of the nutritional strategy of the fungus after invasion of the host. While necrotrophic fungi (for example *Phytophthora infestans, Botrytis cinerea*) rapidly kill the host tissue and then live saprophytically, biotrophic and hemibiotrophic fungi infect the host plant without killing it, or parts of it, for a certain period.

Fungal species which live biotrophically and hemibiotrophically do not kill the tissue of the host plant immediately, but form a fungal mat or spore cushion on the leaf surface which can be observed as whitish, yellowish or brownish changes of the leaf surface. Representatives of leaf diseases caused by biotrophic or hemibiotrophic fungi include leaf spot diseases, rust diseases and diseases which are caused by powdery mildews.

Economically significant leaf spot diseases include *Helminthosporium* spp. in corn or *Septoria* sp. in cereals and vegetable plants. Pathogens of the genus *Puccinia* sp. should be highlighted in the case of rust diseases, which cause dwarf rust in barley, black rust in wheat, asparagus rust, leek rust and rust diseases in many other cultivated plant species. Furthermore, a rust disease in soybeans, which is caused by the pathogen *Phakopsora pachyrhizi*, is of enormous economic significance. What is referred to as Asiatic soybean rust (SBR; *Phakopsora pachyrhizi* Syd.) leads to loss of yields in soybeans (*Glycine max* (L.) Merr.), in particular in areas in which the disease is endemic and there is a lack of controlling measures. Yield losses of up to 80% have been reported in trials in Asia, 60% in Brazil and Paraguay and up to 27% in test fields and 60% in a commercial field in the United States. The first line of defence in controlling soybean rust is the timely use of fungicides. In test areas and on commercial soybean fields in regions of Brazil and the United States, fungicides which consist of triazoles, strobilurins and mixtures thereof have proved to be the most effective method for controlling soybean rust. Despite the efficacy of fungicides in controlling soybean rust, the intensive use of fungicides, in particular of fungicides with a single mode of action, may lead to pathogen-resistant populations, which makes control in subsequent harvest seasons more difficult. Thus, for example, it has been reported that some triazole fungicides are ineffective in controlling soybean rust in fields.

In the context of integrated plant protection, biological plant protection agents constitute an environmentally friendly alternative to chemical fungicides, because they often have a complex mode of action which counteracts a rapid build-up of resistance in the pathogen.

Recently, many different species of microorganisms have been registered globally as an active substance in plant protection agents, but none have been registered which are based on an endophytic bacterium of the species *Kosakonia radicincitans.*

OBJECTIVE AND AIM OF THE INVENTION

The objective of the invention is to develop an environmentally friendly, effective agent against phytopathogenic fungi which is based on defined biological factors.

The aim of the invention is to provide an agent for the prevention and treatment of fungal leaf diseases of cultivated plants which are caused by biotrophic or hemibiotrophic fungi such as the pathogens of leaf spot diseases, for example *Septoria* sp., of rust diseases, for example cereal and vegetable rust (*Puccinia* sp.), of soybean rusts (*Phakopsora pachyrhizi*), or of diseases of the leaf caused by true or false powdery mildews, for example *Peronospora* sp. or *Plasmopara* sp.

DESCRIPTION OF THE INVENTION

The subject matter of the invention is defined in the claims.

In particular, the present invention concerns the preparation and use of an agent for the prevention and treatment of leaf diseases in plants caused by living biotrophic and hemibiotrophic fungal pathogens, wherein the agent contains the bacterium *Kosakonia radicincitans.*

The core concept of the invention is the use of the endophytic bacterium of the species *Kosakonia radicincit-*

*ans* as a seed stock and leaf treatment agent for the prevention and control of fungal leaf diseases caused by biotrophic and hemibiotrophic fungal species, in particular pathogens of leaf spot diseases, for example *Septoria* sp., of rust diseases, for example cereal and vegetable rust (*Puccinia* sp.), of soybean rusts (*Phakopsora pachyrhizi*), of leaf diseases caused by true or false powdery mildews, for example *Peronospora* sp. or *Plasmopara* sp., on the leaves of cultivated plants.

It has surprisingly been discovered that a treatment of the seed stock or the leaves with an agent containing the bacterium *Kosakonia radicincitans*, with the accession number DSM 16656 from the Leibniz Institute DSMZ, has a preventative effect against infection with biotrophic phytopathogenic fungi such as soybean rust, for example.

The present invention concerns an agent for the prevention and treatment of leaf diseases in plants caused by living biotrophic and hemibiotrophic fungal pathogens, wherein the agent contains the bacterium *Kosakonia radicincitans.*

The agent in accordance with the invention contains the bacterium *Kosakonia radicincitans* as the active substance. Preferably, the bacterium comprises or consists of *Kosakonia radicincitans* from the strain with the accession number DSM16656. The bacterium *Kosakonia radicincitans* may be cultured both in liquid culture as well as in solid culture. Methods for culturing the bacterium *Kosakonia radicincitans* are known to the person skilled in the art.

The agent in accordance with the invention may contain the bacterium *Kosakonia radicincitans* in any form; preferably, the agent contains the bacterium *Kosakonia radicincitans* in a form which is stable upon storage and which enables reproduction or (re)culture of the bacterium. In particular, the agent may contain the bacterium *Kosakonia radicincitans* in the form of its cells and/or in the form of components of its liquid or solid culture. By using live bacterial cells, long-lasting effects may be obtained which are based on the ability of the bacterium to colonize the interior of the plant. The bacterial cells are found in large quantities in the liquid or solid culture of *Kosakonia radicincitans*, which allows for simple and cost-effective production of the agent in accordance with the invention.

The agent in accordance with the invention may be formulated as a dry preparation or as a liquid preparation. The agent itself may also be present as a solid for subsequently taking it up into solution in order to use the agent for the treatment of seeds/seed stock or parts of plants. As an alternative, the agent may also be present in the liquid form, wherein the material may contain the bacterium *Kosakonia radicincitans* in a concentration which is suitable for use of the agent in the prevention and treatment of leaf diseases caused by living biotrophic and hemibiotrophic fungal pathogens. The agent may also contain the bacterium *Kosakonia radicincitans* in a higher concentration. In this case, the agent is provided as a concentrate which is diluted to the intended concentration prior to the desired use.

In addition, the agent in accordance with the invention may also have other active substances and/or auxiliary materials.

Examples of auxiliary materials may be materials which support the formulation of the agent, increase the stability upon storage or facilitate handling. Thus, for example, the agent in accordance with the invention may contain one or more auxiliary materials which preferably include sugar, skimmed milk powder, glycerol, CaO, MgO, $SiO_2$ or a combination of several of said auxiliary materials.

The additional active substances contained in the agent may be further chemical compounds or biological materials such as further microorganisms, for example. In a preferred embodiment, the agent in accordance with the invention contains further microorganisms such as, for example, additional bacteria in the form of spores and/or in the form of components of the respective liquid or solid culture. Particularly preferably, the agent in accordance with the invention contains additional bacteria of the species *Bacillus velezensis, Bacillus atrophaeus, Bacillus pumilus, Bacillus simplex, Bacillus licheniformis* and/or *Trichoderma* sp.

The present invention also concerns the use of the agent in accordance with the invention for the prevention and treatment of leaf diseases in plants caused by living biotrophic and hemibiotrophic fungal pathogens.

For the purposes of the present invention, the term "leaf diseases" should be understood to mean those diseases of plants which are caused by living biotrophic and hemibiotrophic fungi and which exhibit optically visible symptoms or changes in the leaves such as, for example, brown stains, lesions and/or accumulations of fungal spores.

The leaf disease which can be treated by the agent in accordance with the invention is preferably a leaf spot disease, a rust disease and/or a disease of leaves caused by true or false powdery mildews.

What is common to the leaf diseases which are to be treated by the agent in accordance with the invention is that it is caused by living biotrophic and hemibiotrophic fungi.

Thus, for example, rust diseases in plants are as a rule caused by fungi of the order Pucciniales (rust fungi), preferably by fungi of the genuses *Puccinia, Phakopsora, Hemileia*, Aecidium and *Uromyces*, particularly preferably of the genuses *Puccinia* and *Phakopsora*, more particularly preferably of the species *Phakopsora pachyrhizi, Puccinia* sp. (in particular *Puccinia graminis* (grain rust), *Puccinia sorghi* (corn rust), *Puccinia striiformis* (yellow rust), *Puccinia* triticina (brown rust in wheat).

As a rule, a leaf spot disease is caused by fungi of the order Pleosporales or Capnodiales, preferably by fungi of the genuses *Septoria* and *Stagonospora*, more particularly preferably of the species *Septoria* sp. (in particular *Septoria tritici, Septoria lycopersici, Stagnospora nodorum*).

As a rule, true powdery mildew is caused by fungi of the order Erysiphales, preferably by fungi of the species Blumeria, *Erysiphe, Microsphaera*, Oidium and *Podosphaera*, more particularly preferably of the species Blumeria *graminis, Erysiphe* sp. (in particular *Erysiphe betae, Erysiphe communis, Erysiphe cruciferarum, Erysiphe graminis, Erysiphe* necator).

Examples of fungi which can cause false powdery mildew are: fungi of the order Peronosporales, preferably fungi of the genuses *Peronospora* and *Plasmopora*, more particularly preferably of the species *Peronospora* sp. (in particular *Peronospora tabacina*) and *Plasmopora* sp. (in particular *Plasmopora viticola*).

Preferably, the agent in accordance with the invention for the prevention and treatment of leaf diseases is used in plants wherein the leaf disease is caused by a fungal pathogen selected from the order Pucciniales (rust fungi), Erysiphales, Peronosporales, Pleosporales and Capnodiales; preferably from the genuses *Puccinia, Phakopsora, Hemileia, Aecidium, Uromyces, Septoria, Stagonospora, Blumeria, Erysiphe, Microsphaera, Oidium, Podosphaera, Peronospora* and *Plasmopora*. Particular preferably, the agent in accordance with the invention for the prevention and treatment of leaf diseases is used in plants wherein the fungal pathogen is selected from *Phakopsora pachyrhizi, Puccinia* sp. (in particular *Puccinia graminis* (grain rust), *Puccinia sorghi* (corn rust), *Puccinia striiformis* (yellow rust), *Puc-*

*cinia* triticina (brown rust in wheat), *Septoria* sp. (in particular *Septoria tritici, Septoria lycopersici, Stagnospora nodorum*), Blumeria *graminis, Erysiphe* sp. (in particular *Erysiphe betae, Erysiphe communis, Erysiphe cruciferarum, Erysiphe graminis, Erysiphe necator*), *Peronospora* sp. (in particular *Peronospora tabacina*) and *Plasmopora* sp. (in particular *Plasmopora viticola*).

When using the agent in accordance with the invention for the prevention and treatment of leaf diseases in plants, the agent is used in a manner such that the seed stock or a portion of the plant to be treated is brought into contact with the agent. This may be achieved by any method which brings the agent into contact with the seed stock or a portion of the plant to be treated in a manner such that the bacterium *Kosakonia radicincitans* remains on a portion of the surface of the seed stock or the portion of the plant or is taken up, at least in part, by the seed stock or by the portion of the plant to be treated. In particular, the agent in accordance with the invention may be used for watering, for drip irrigation, for immersion, for addition to the nutrient solution in hydroponic systems, as a substrate admixture or for leaf spraying.

The present invention concerns a method for the prevention and treatment of leaf diseases in plants caused by living biotrophic and hemibiotrophic fungal pathogens, wherein an agent in accordance with the invention is used. The method in accordance with the invention is in particular characterized in that the seed stock to be treated or a component of the plant to be treated is brought into contact with the agent. This contacting may be carried out in a wide variety of manners. Thus, the seed stock may be coated with the agent in accordance with the invention or wetted or immersed in a liquid solution containing the agent in accordance with the invention. The plant to be treated may, for example, be watered with a liquid solution containing the agent in accordance with the invention, or above-ground portions of the plant, such as leaves and/or stems, for example, may be sprayed or splashed with a solution of this type.

The present invention concerns seed stock which has been treated with an agent in accordance with the invention. Thus, the seed stock in accordance with the invention may, for example, be brought into contact with a solution containing the agent in accordance with the invention (for example by immersion, spraying or coating). Preferably, the seed stock has the agent in accordance with the invention on at least a portion of its external surface. In the context of the present invention, the term “seed stock” should be understood to mean dormant, generative reproductive organs such as seeds, fruit, pseudo-fruit, multiple fruit or parts thereof. The seed stock contains the entirety of the germinal material of the plant in question which is generated upon fertilization.

Finally, the present invention also concerns a plant, wherein parts of the plant have been brought into contact with an agent in accordance with the invention, preferably, the plant has the agent in accordance with the invention on at least a portion of its external surface; particularly preferably, the plant has the agent in accordance with the invention on at least a portion of the external surface of its leaves.

FIGURES

FIG. 1: Efficacy test for *Kosakonia radicincitans* as seed stock treatment against *phakopsora* infection of the primary leaf of *Glycine max*. Reduction of the infected area of the leaf (rust pustules, lesions and chlorosis) after treatment of the seed stock with *Kosakonia radicincitans*. The control, with 60% of the leaf surface infected, had significantly more infection than the leaves of the soya plants the seed stock of which had been treated with *Kosakonia radicincitans.*

Figure 2:
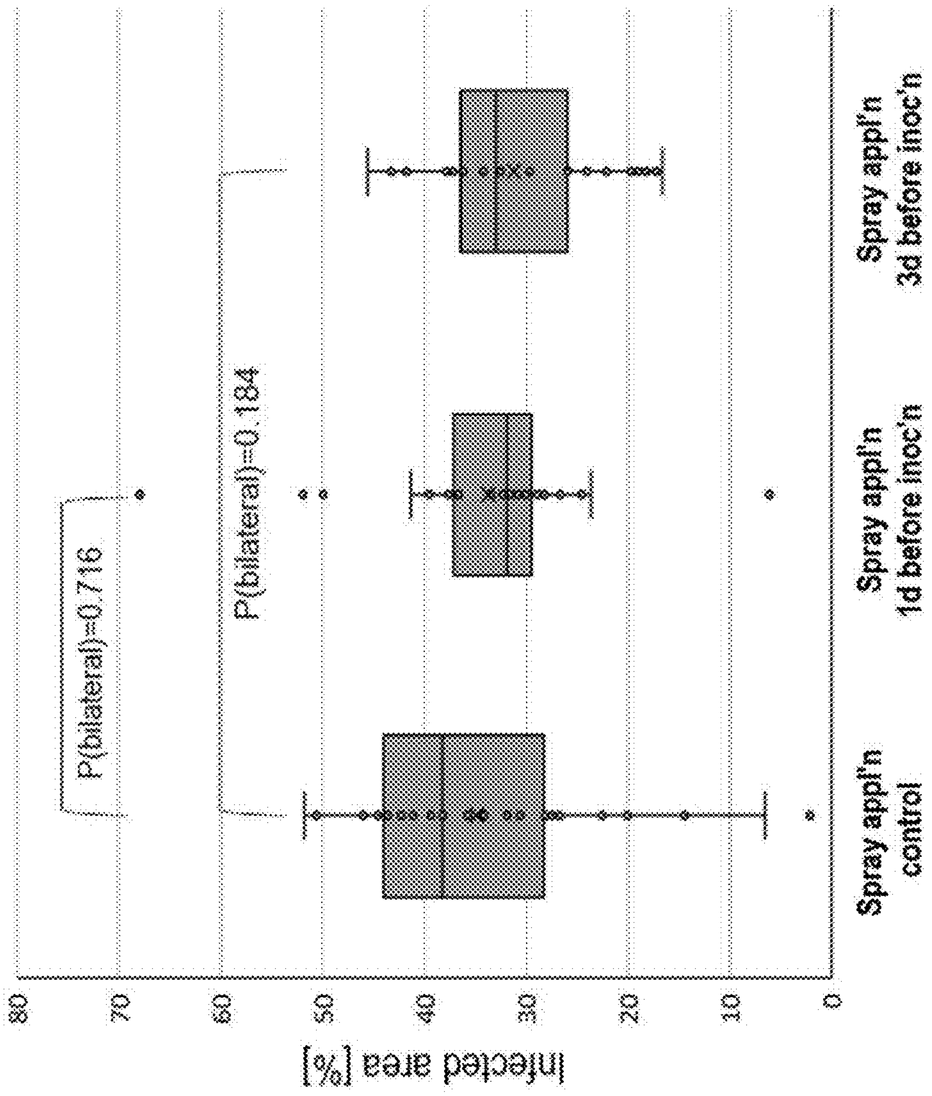

FIG. 2: Efficacy test for *Kosakonia radicincitans* as leaf application against *phakopsora* infection of the primary leaf of *Glycine max.* as a leaf spray one day or 3 days before artificial infection of the leaf. The control, with 38% of the leaf surface infected, was generally more infected than the leaves of the soya plants treated by spraying the leaves with *Kosakonia radicincitans.*

The invention will be described in more detail in the exemplary embodiments below.

EXEMPLARY EMBODIMENTS

Efficacy Against Soybean Rust:

In order to test the efficacy against soybean rust, the *Kosakonia radicincitans* strain DSM16656 was incubated in 150 mL of SNB medium for 8 h at 200 rpm and harvested by centrifuging. The bioslurry obtained in this manner was taken up in 10 mL of sterile 0.9% NaCl solution and the soybean seed stock (*Glycine max* var. Viola) was rocked vigorously for 1 min at ambient temperature. The seed stock was then redried for 15 min in a stream of air at ambient temperature and afterwards placed on moist 3MM Whatman paper for 3 days in order to germinate. On the third day, germinated seedlings were planted out into pots with Fruhstorfer soil and placed in the greenhouse. 9 days after planting out, the inoculation of the primary leaves with the pathogen *Phakopsora pachyrhizi* was carried out. Classification scoring of the lesions was carried out 12 days after infection of the leaves. For the application to the leaves, per plant, 10E+08 of live *Kosakonia radicincitans* cells were applied by leaf spraying one or three days prior to infection of the primary leaf with *Phakopsora pachyrhizi.*

The seed stock application of *Kosakonia radicincitans* in soybeans exhibited a significant effect against soybean rust (FIG. 1). The primary infection with *Phakopsora pachyrhizi* was reduced by 12% under unnaturally high infection pressure under laboratory conditions. In this regard, a significant reduction in rust pustules, lesions and chlorosis was observed on the surface of the infected primary leaves.

A spray application to the leaves showed that independently of the time of application, one or three days before infection of the leaves, there was still no significant effect (FIG. 2), but a clear trend to a reduction in the infected surface of the leaf (rust pustules, lesions and chlorosis). It can be seen that the treatment three days before inoculation of the fungus tended to have a better effect than the treatment one day before inoculation.

In addition to improved disease resistance of the soybean plants, the results show that in the case of a seed stock treatment, a sufficient protective effect against infection with Asiatic soybean rust can be obtained (FIG. 1). Spraying the leaves one or three days before artificial infection showed a trend towards disease prevention (FIG. 2). The results of seed stock treatment and leaf treatment enable the conclusion to be drawn that the bacterium firstly has to become established in the plant before its preventative effect can be deployed. For this reason, it may be concluded that the endophytic lifestyle of the bacterium offers general protection against phytopathogenic fungi which have a biotrophic or hemibiotrophic lifestyle, because they have to compete with *Kosakonia radicincitans* for the habitat inside the plant and therefore it is more difficult for them to become established in the host plant.

The invention claimed is:

1. A method of using an agent for prevention and treatment of leaf diseases in a plant or a seed stock of the plant, wherein the method comprises:

preparing a solid form of the agent, the agent comprising bacterium *Kosakonia radicincitans*, the preparing the solid form of the agent comprising incubating the agent and harvesting a bioslurry including the agent by centrifuging;

taking the solid form of the agent up in a solution; and treating the plant or seed stock of the plant with the solution, wherein the plant comprises a soybean plant having a leaf disease comprising soybean rust caused by an obligately biotrophic fungal pathogen *Phakopsora pachyrhizi*.

2. The method as claimed in claim 1, wherein the bacterium *Kosakonia radicincitans* comprises a strain with an accession number DSM16656.

3. The method as claimed in claim 1, wherein the agent comprises at least one of:

a first form of the bacterium *Kosakonia radicincitans* including bacterial cells; and a second form of the bacterium *Kosakonia radicincitans* including components of a liquid or a solid culture.

4. The method as claimed in claim 1, wherein the agent comprises an auxiliary material comprising at least one of sugar, skimmed milk powder, glycerol, CaO, or MgO, $SiO_2$.

5. The method as claimed in claim 1, wherein the agent additionally comprises at least one of *Bacillus velezensis, Bacillus atrophaeus, Bacillus pumilus, Bacillus simplex, Bacillus licheniformis* or *Trichoderma* sp.

6. The method of claim 1, wherein the agent is used for at least one of a seed stock treatment, watering, drip irrigation, immersion, an addition to a nutrient solution in hydroponic systems, a substrate admixture, or leaf spraying.

* * * * *